(12) United States Patent
Zimmerman et al.

(10) Patent No.: US 7,790,677 B2
(45) Date of Patent: Sep. 7, 2010

(54) INSULIN PRODUCTION METHODS AND PRO-INSULIN CONSTRUCTS

(75) Inventors: Ronald E. Zimmerman, Greenwood, IN (US); David John Stokell, Indianapolis, IN (US)

(73) Assignee: Elona Biotechnologies, Greenwood, IN (US)

( * ) Notice: Subject to any disclaimer, the term of this patent is extended or adjusted under 35 U.S.C. 154(b) by 157 days.

(21) Appl. No.: 11/725,731

(22) Filed: Mar. 20, 2007

(65) Prior Publication Data
US 2008/0146492 A1   Jun. 19, 2008

Related U.S. Application Data

(60) Provisional application No. 60/874,655, filed on Dec. 13, 2006.

(51) Int. Cl.
*A61K 38/28*   (2006.01)
*C07K 14/62*   (2006.01)

(52) U.S. Cl. .......................................... 514/3; 530/303
(58) Field of Classification Search ........................ None
See application file for complete search history.

(56) References Cited

U.S. PATENT DOCUMENTS

| 4,916,212 A | 4/1990 | Markussen et al. |
| 5,962,267 A | 10/1999 | Shin et al. |
| 6,777,207 B2 | 8/2004 | Kjeldsen et al. |

FOREIGN PATENT DOCUMENTS

EP   0 055 945   7/1982

OTHER PUBLICATIONS

Johansson et al. Effects of C-peptide on blood flow, capillary diffusion capacity and glucose utilization in the exercising forearm of Type 1 (insulin-dependent) diabetic patients. Diabetologia 35:1151-1158 (1992).*
Johansson et al. The influence of human C-peptide on renal function and glucose utilization in Type 1 (insulin-dependent) diabetic patients. Diabetologia 35:121-128 (1992).*
Ido et al. Prevention of vascular and neural dysfunction in diabetic rats by C-peptide. Science 277:563-566 (1997).*
Forst et al. Biological activity of C-peptide on the skin microcirculation in patients with insulin-dependent diabetes mellitus. J. Clin. Invest. 101/10:2036-2041 (May 1998).*

(Continued)

*Primary Examiner*—Marianne P Allen
*Assistant Examiner*—Regina M DeBerry
(74) *Attorney, Agent, or Firm*—K&L Gates LLP

(57) ABSTRACT

Novel pro-insulin having specific amino acid and/or nucleic acid modifications suitable for improved methods of insulin production are provided. Novel and highly efficient processes for preparing the pro-insulin preparations and preparations containing them are also disclosed. The novel pro-insulin preparations may be converted into human insulin useful in therapeutic preparations. Novel peptides of the C-peptide, and N terminus, including RREAEALQVGQVELGGGP-GAGSLQPLALEGSLQAR (SEQ ID NO: 32), and MHHH-HHHGGR (SEQ ID NO: 2) respectively are provided, as well as the unique nucleic acid molecules encoding them.

4 Claims, 6 Drawing Sheets

OTHER PUBLICATIONS

Sjoquist et al. Effects of C-peptide on renal function at the early stages of experimental diabetes. Kidney International 54:758-764 (1998).*

Wahren et al. Role of C-peptide in human physiology. Am. J. Physiol. Endocrinol. Metab. 278:E759-E768 (2000).*

Kitamura et al. Pro-insulin C-peptide rapidly stimulates mitogen-activated protein kinases in Swiss 3T3 fibroblast: requirement of the protein kinase C, phosphoinositide 3-kinase and pertussis toxin-sensitive G-protein. Biochem. J. 355:123-129 (2001).*

Chance (1981), Peptides: Proceedings of the 7th American Peptide Chemistry Symposium, 721-728 (Rich, D. and Gross, E. eds.).

Chan (1981), P.N.A.S., U.S.A., 78:5401-5404.

Chang (1998), Bio Hen: J. 329: 631-635.

Frank (1981), Peptides: Proceedings of the 7th American Peptide Chemistry Symposium, 729-739 (Rich, D. and Gross, E. eds.).

Thim (1986), P.N.A.S., U.S.A., 83: 6766-6770.

* cited by examiner

CHROM TYPE: HPLC CHANNEL: 1

ACQUISILAION METHOD: INSULIN C18 23-25% ACNgrad
COLUMN TYPE: DIAZEM C4A  4.6 X 15cm
PUMP A TYPE: L-7100
  SOLVENT A: 20% ACN, 0.2%PHOS, 200mM NaSul
  SOLVENT B: 25% ACN, 0.2%PHOS, 100Mm NaSul
y:

METHOD DESCRIPTION:

CHROM TYPE: HPLC CHANNEL: 1

PEAK QUANTITATION: AREA
CALCULATION METHOD: AREA%

| NO. | RT | AREA | CONC 1 | BC | HEIGHT |
|---|---|---|---|---|---|
| 1 | 6.40 | 28991 | 0.049 | BB | 1286 |
| 2 | 8.82 | 33703 | 0.056 | BB | 1030 |
| 3 | 11.01 | 81975 | 0.137 | BB | 2275 |
| 4 | 13.30 | 251286 | 0.421 | BB | 8801 |
| 5 | 14.77 | 65282 | 0.109 | BB | 2119 |
| 6 | 16.89 | 110335 | 0.185 | BV | 2306 |
| 7 | 18.49 | 1029422 | 1.724 | VV | 17168 |
| 8 | 20.64 | 417663 | 0.700 | VB | 6333 |
| 9 | 25.15 | 22565 | 0.038 | BB | 414 |
| 10 | 28.67 | 647054 | 1.084 | MC | 2478 |
| 11 | 31.23 | 22263393 | 37.291 | MC | 228478 |

CHROM TYPE: HPLC CHANNEL: 1

ACQUISILAION METHOD: INSULIN C18 23-25% ACNgrad
COLUMN TYPE: DIAZEM C4A 4.6 X 15cm
PUMP A TYPE: L-7100
  SOLVENT A: 20% ACN, 0.2%PHOS, 200mM NaSul
  SOLVENT B: 25% ACN, 0.2%PHOS, 100Mm NaSul

METHOD DESCRIPTION:

CHROM TYPE: HPLC CHANNEL: 1

PEAK QUANTITATION: AREA
CALCULATION METHOD: AREA%

| NO. | RT | AREA | CONC 1 | BC | HEIGHT |
|---|---|---|---|---|---|
| 1 | 6.89 | 2070 | 0.024 | BB | 122 |
| 2 | 10.99 | 6906 | 0.082 | BB | 273 |
| 3 | 14.43 | 50139 | 0.592 | BB | 1241 |
| 4 | 15.72 | 33030 | 0.390 | BB | 1223 |
| 5 | 16.71 | 1746 | 0.021 | BB | 104 |
| 6 | 19.62 | 97354 | 1.150 | BB | 1493 |
| 7 | 23.41 | 9047 | 0.107 | BB | 138 |
| 8 | 28.77 | 3775335 | 44.608 | BV | 16675 |
| 9 | 35.60 | 3656788 | 43.207 | VB | 12285 |
| 10 | 46.73 | 831027 | 9.819 | BB | 4263 |

INSULIN PRODUCTION METHODS AND PRO-INSULIN CONSTRUCTS

CROSS-REFERENCE TO RELATED APPLICATIONS

This application makes reference to co-pending U.S. Provisional Patent Application Ser. No. 60/874,655, filed Dec. 13, 2006, the entire disclosure and contents of which are hereby incorporated by reference.

BACKGROUND

1. Field of the Invention

The present invention in a general and overall sense relates to the field of recombinant proteins and peptides. The invention also relates to the field of molecular processes and methods for producing recombinant proteins particularly methods that employ E. coli as an expression vehicle. The invention also relates to compositions and methods for preparing pro-insulin, insulin, and both of these alone or in combination with each other and with other compositions.

2. Background of the Related Art

Insulin is a polypeptide hormone secreted by beta-cells of the pancreas. This hormone is made up of two polypeptide chains, an A-chain of 21 amino acids, and a B-chain of 30 amino acids. These two chains are linked to one another in the mature form of the hormone by two interchain disulfide bridges. The A-chain also features one intra-chain disulfide bridge.

Insulin is a hormone that is synthesized in the body in the form of a single-chain precursor molecule, pro-insulin. Pro-insulin is a molecule comprised of a prepeptide of 24 amino acids, followed by the B-chain peptide, a C-peptide of 35 amino acids, and an A-chain peptide. The C-peptide of this precursor insulin molecule contains the two amino acids, lysine-arginine (LR) at its carboxy end (where it attaches to the A-chain), and the two amino acids, arginine-arginine (RR) at its amino end (where it attaches to the B-chain). In the mature insulin molecule, the C-peptide is cleaved away from the peptide so as to leave the A-chain and the B-chain connected directly to one another in its active form.

Molecular biology techniques have been used to produce human pro-insulin. In this regard, three major methods have been used for the production of this molecule. Two of these methods involve Escherichia coli, with either the expression of a large fusion protein in the cytoplasm (Chance et al. (1981), and Frank et al (1981) in Peptides: Proceedings of the 7$^{th}$ American Peptide Chemistry Symposium (Rich, D. and Gross, E., eds.), pp. 721-728, 729-739, respectively, Pierce Chemical Company, Rockford, Ill.), or the use of a signal peptide to enable secretion into the periplasmic space (Chan et al (1981) P.N.A.S., U.S.A., 78:5401-5404). A third method utilizes yeast, especially Saccharomyces cerevisiae, to secrete the insulin precursor into the medium (Thim, et al. (1986), P.N.A.S., U.S.A., 83:6766-6770).

Chance et al. report a process for preparing insulin by producing each of the A and B chains of insulin in the form of a fusion protein by culturing E. coli that carries a vector compromising a DNA encoding the fusion protein, cleaving the fusion protein with cyanogen bromide to obtain the A and the B chains, sulfonating the A and B chains to obtain sulfonated chains, reacting the sulfonated B chain with an excess amount of the sulfonated A chain; and then purifying the resultant products to obtain insulin. Drawbacks associated with this process are that it requires two fermentation processes and the requirement of a reaction step for preparing the sulfonated A chain and the sulfonated B chain. This results in a low insulin yield.

Frank et al. described a process for preparing insulin in the form of a fusion protein in E. coli. In this process, pro-insulin is produced in the form of a fusion protein by culturing E. coli which carries a vector comprising a nucleic acid sequence (DNA) encoding for the fusion protein, cutting the fusion protein with cyanogens bromide to obtain pro-insulin, sulfonating the pro-insulin and separation of the sulfonated pro-insulin, refolding the sulfonated pro-insulin to form correct disulfide bonds, treating the refolded pro-insulin with trypsin and carboxypeptidase B, and then purifying the resultant product to obtain insulin. However, the yield of the refolded pro-insulin having correctly folded disulfide bonds is reported to sharply decrease as the concentration of the pro-insulin increases. This is allegedly due to, at least among other reasons, to misfolding of the protein, and some degree of polymerization being involved. Hence, the process entails the inconvenience of using laborious purification steps during the recovery of pro-insulin.

Thim et al. report a process for producing insulin in yeast, Sacchromyces cerevisiae. This process has the steps of producing a single chain insulin analog having a certain amino acid sequence by culturing Sacromyces cerevisiae cells, and isolating insulin there from through the steps of: purification, enzyme reaction, acid hydrolysis and a second purification. This process, however, results in an unacceptably low yield of insulin.

The role of the native C-peptide in the folding of pro-insulin is not precisely known. The dibasic terminal amino acid sequence at both ends of the C-peptide sequence has been considered necessary to preserve the proper processing and/or folding of the pro-insulin molecule to insulin.

Other amino acids within the within the C-peptide sequence, however, have been modified with some success. For example, Chang et al. (1998) (Biochem. J., 329:631-635) described a shortened C-peptide of a five (5) amino acid length, —YPGDV—(SEQ ID NO: 1), that includes a preserved terminal di~basic amino acid sequence, RR at one terminal end, and LR at the other terminal end, of the peptide. Preservation of the dibasic amino acid residues at the B-chain-C peptide (B-C) and C-peptide-A-chain junctures is taught as being a minimal requirement for retaining the capacity for converting the pro-insulin molecule into a properly folded mature insulin protein. The production of the recombinant human insulin was described using E. coli with a shortened C-peptide having a dibasic amino acid terminal sequence.

One of the difficulties and/or inefficiencies associated with the production of recombinant insulin employing a pro-insulin construct having the conserved, terminal di-basic amino acid sequence in the C-peptide region is the presence of impurities, such as Arg-insulin, in the reaction mixture, once enzymatic cleavage to remove the C-peptide is performed. This occurs as a result of misdirected cleavage of the pro-insulin molecule so as to cleave the C-peptide sequence away from the A-chain at this juncture, by the action of trypsin. Trypsin is a typical serine protease, and hydrolyses a protein or peptide at the carboxyl terminal of an arginine or lysine residue (Enzymes, pp. 261-262 (1979), ed. Dixon, M. & Webb, E. C. Longman Group Ltd., London). This unwanted hydrolysis results in the unwanted ARG-AO-insulin by-product, and typically constitutes about 10% of the reaction yield. Hence, an additional purification step is required. The necessity of an additional purification step makes the process much more time consuming, and thus expensive, to use. Moreover, an additional loss of yield may be expected from the necessity of this additional purification step.

Others have described the use of pro-insulin constructs that do not have a conserved terminal dibasic amino acid sequence of the C-peptide region. For example, U.S. Pat. No. 6,777,207 (Kjeldsen et al.) relates to a novel pro-insulin peptide construct containing a shortened C-peptide that includes the two terminal amino acids, glycine-arginine or glycine-lysine at the carboxyl terminal end that connects to the A-chain of the peptide. The B-chain of the pro-insulin construct described therein has a length of 29 amino acids, in contrast to the native 30 amino acid length of the native B-chain in human insulin. The potential effects of this change to the native amino acid sequence of the B-chain in the human insulin produced are yet unknown. Methods of producing insulin using these pro-insulin constructs in yeast are also described. Inefficiencies associated with correct folding of the mature insulin molecule when yeast utilized as the expression host, render this process, among other things, inefficient and more expensive and time consuming to use. In addition, yeast provides a relatively low insulin yield, due to the intrinsically low expression levels of a yeast system as compared to *E. coli.*

As evidenced from the above review, a present need exists for a more efficient process for production of human insulin that is efficient eliminates currently necessary purification steps, and that at the same time improves and/or preserves acceptable production yield requirements of the pharmaceutical industry.

The above references are incorporated by reference herein where appropriate for appropriate teachings of additional or alternative details, features and/or technical background.

SUMMARY OF THE INVENTION

The present invention provides novel pro-insulin compositions. These compositions may be further defined as comprising a peptide, an amino acid sequence, or a nucleic acid sequence encoding a modified C-peptide or a modified pro-insulin molecule, or a pharmaceutical preparation of these peptides in a pharmaceutically acceptable carrier solution and/or diluent. Among other distinguishing features, the novel pro-insulin as disclosed herein includes a unique non-di-basic amino acid sequence at one or both of its C-peptide terminal ends. In some embodiments, the constructs are described as an N-terminal multiple His-tagged pro-insulin construct. In particular embodiments, the N-terminal multiple His-tagged construct comprises a 6-histidine (SEQ ID NO: 24) N-terminal tag. In some embodiments, the construct comprises a structure as defined in Formula 1 or Formula II:

```
Formula I:                              (SEQ ID NO: 2)
MHHHHHHGGR - X1 - C peptide - X2,
or Formula II:                             (SEQ ID NO: 2)
MHHHHHHGGR - X1 - modified C peptide - X2
``` wherein X1 comprises an insulin B Chain, and wherein X2 comprises an insulin A Chain. In the Formula II construct, the modified C peptide is defined as a sequence having a non-dibasic (such as AR) amino acid sequence at a terminal end of the modified C peptide component that is adjacent the X2 component (insulin A chain) and/or a modification (such as RA) located adjacent the X1 component (insulin B chain) in the construct as depicted in Formula II.

The invention in particular aspects may be further defined as providing a novel pro-insulin composition. This composition may be further defined as comprising a peptide, an amino acid sequence, or nucleic acid sequence encoding the pro-insulin. The purified and transformed pro-insulin, comprises a pharmaceutical preparation formulated with a pharmaceutically acceptable carrier solution and/or diluent.

The invention also provides a novel process for producing highly purified insulin that is more efficient than current techniques. In particular aspects, the process employs bacteria, such as *E. coli.*

The process presents many advantages, among them the advantage of reducing and/or eliminating the presence of unwanted and contaminating cleavage by-products characteristic of conventional manufacturing processes for producing recombinant human insulin in *E. coli.* Previously undesirable by-products evident in yield mixtures using conventional methods of producing recombinant human insulin included, by way of example, the production of an unwanted cleavage product, ARG-A0-insulin. A highly efficient process for the production of recombinant human insulin is presented that reduces and/or eliminates the presence of this and other unwanted and undesirable cleavage by-products, and that further presents the advantages of eliminating several time consuming, expensive, purification steps. A process having fewer technician-assisted steps is thus devised, and illustrates the additional advantage of eliminating the degree of inconsistency and/or error associated with technician assisted steps in the manufacturing process.

In some embodiments, the preparations comprise a pharmaceutically acceptable preparation comprising recombinant human insulin and being essentially free of pro-insulin.

An object of the invention is to solve at least the above problems and/or disadvantages and to provide at least the advantages described hereinafter.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

Figure 1:
FIG. 1, according to one aspect of the invention, presents a gel showing expression of the full length His-tagged/K64A pro-insulin (10.5 KDa) protein. The gel is from the expression product produced from the *E. coli*, BL21 strain, transformed with the above mentioned genes.

The present invention provides novel pro-insulin constructs, C-peptides, and methods for using these in a process to provide high yields of mature recombinant human insulin. The pro-insulin constructs include a novel C-peptide that includes a non-dibasic terminal amino acid sequence at one end.

In particular embodiments, the non-dibasic alanine-arginine (AR) sequence at the carboxyl terminus of the C-chain. The C-terminus of the C-peptide connects to the A-chain of the pro-insulin molecule. Advantageously, the positioning of these particular terminal amino acids in the C-peptide provides for an improved method for producing recombinant human insulin, having fewer steps, improved yields of the recombinant human insulin protein and less contaminating byproducts.

As used in the description of the present inventions the term "connecting peptide" or "C-peptide" is meant the connecting moiety "C" of the B-C-A polypeptide sequence of a single chain pro-insulin molecule. Specifically, in the native human insulin chain, the C-peptide connects to position 30 of the B-chain and position 1 of the A-chain. In the present inventions the A-chain and the B-chain of the pro-insulin constructs retain their native sequences and lengths. The C-peptide constructs disclosed have been modified so as to include different terminal amino acids relative to native C-peptide.

As in native human pro-insulin, the C-peptide constructs of the present invention connect position 30 of the B-chain and position 1 of the A-chain. The single chain pro-insulin molecules of the invention will include three (3) correctly positioned disulphide bridges, as is characteristic of the native human pro-insulin molecule. The amino acid sequence of the B-chain and the A-chain of the pro-insulin constructs, as well as the human insulin products produced by the methods described herein, will have the native amino acid sequence characteristic of native human insulin.

As used in the description of the present invention, the terms "insulin precursor" or "pro-insulin" are described as a single-chain polypeptide in which, by one or more subsequent chemical and/or enzymatic processes, may be converted into human insulin.

As used in the description of the present invention, the term "pro-insulin analog" is defined as a pro-insulin molecule having one or more mutations, substitutions, deletions, and/or additions, of the A, B and/or C chains relative to the native human pro-insulin nucleic acid sequence. The pro-insulin analogs are preferably such wherein one or more of the naturally occurring nucleic acids have been substituted with another nucleic acid within a triplet encoding for a particular amino acid.

The term "a" as used in the description of the present invention is intended to mean "one or more", and is used to define both the singular and plural forms of the item or items to which it references, or to a feature or characteristic to which it refers. The use of the singular or plural in the claims or specification is not intended to be limiting in any way and also includes the alternative form.

The term "about" is intended to be inclusive of and to encompass both an exact amount as well as an approximate amount or range of values or levels of the item, ingredient, element, activity, or other feature or characteristic to which it references. Generally, and in some embodiments, the term "about" is intended to reference a range of values relatively close to the specific numerical value specifically identified. For example, "about 3 grams to about 5 grams" is intended to encompass a measure of in or around a value of 3 grams, concentration values between 3 grams and 5 grams, concentration values in and around 5 grams, as well as concentration values that are exactly 3 grams and exactly 5 grams.

As used in the description of the present process, a high protein concentration of the pro-insulin or insulin product is defined as a protein yield concentration of at least about 3 grams/liter, or between about 3 grams to about 5 grams per liter. The expression yield to be expected may be defined as a protein/peptide yield that is sufficient to detect via polyacrylamide gel electrophoreses (PAGE).

The invention in a general and overall sense relates to an improved process for preparing a heterologous recombinant protein in a prokaryotic host cell. This process is characterized in that it employs a unique recombinant protein that provides a useful and efficiently processed pro-insulin peptide having a unique, modified C-peptide region, as well as a His tagged N-terminal sequence.

By heterologous protein is meant that said protein in said prokaryotic host cell is not native, i.e., it occurs as a protein in peculiar or foreign (i.e., not native to) the host prokaryotic cell.

"Recombinant" means produced or modified by molecular-biological methods.

As used in the description of the present invention, the term "heterologous recombinant protein" is defined as any protein known to the skilled person in the molecular biological arts, such as, for example, insulin, pro-insulin, C-peptide, and proteins containing these together with any other protein or peptide fragment.

Prokaryotic host cells may be any host cells known to the skilled artisan in the molecular biological arts, and by way of example, *Escherichia coli*. Such types of cells available form public collections and useful in the practice of the present invention include, by way of example, the Deutsche Sammlung von Mikrooganismen and Zellkulturen GmbH, raunschweig, Germany, e.g., *E. coli* Strain K12 JM107 (DSM 3950).

Proteins and peptides are chains of amino acids linked by peptide bonds, which in the case of proteins give a defined structure that is typically required for activity. Peptides are chains of amino acids which may or may not have activity or a defined structure.

Human Insulin Amino Acid sequence: Sequence of amino acids which make up the native insulin A and B chains.

```
                                              (SEQ ID NO: 3)
FVNQHLCGSHLVEALYLVCGERGFFYTPKTGIVEQCCTSICSLYQLENY
CN
```

The following reference table provides the triplet codons corresponding to each of the various amino acids that are used in the description of the present invention. As will be understood by those of skill in the art, the amino acid that may be used in any particularly defined position as part of any of the peptide, protein, or constructs otherwise defined herein by reference to a particular nucleotide triplet base pair may be encoded by a number of different nucleotide triplets that function to encode the same amino acid. For example, where the amino acid of the sequence defined herein is alanine (Ala, or A), the triplet codon of nucleic acids that may encode for this amino acids are: GCT, GCC, GCA, or GCG. The following table illustrates this definition of variables at and substitutions as can be applied to all of the naturally occurring amino acids sequences of the disclosure.

| | Second Position | | | | |
|---|---|---|---|---|---|
| | U | C | A | G | |
| U | UUU ] Phe<br>UUC ]<br>UUA ] Leu<br>UUG ] | UCU ]<br>UCC ] Ser<br>UCA ]<br>UCG ] | UAU ] Tyr<br>UAC ]<br>UAA Stop<br>UAG Stop | UGU ] Cys<br>UGC ]<br>UGA Stop<br>UGG Trp | U<br>C<br>A<br>G |
| C | CUU ]<br>CUC ] Leu<br>CUA ]<br>CUG ] | CCU ]<br>CCC ] Pro<br>CCA ]<br>CCG ] | CAU ] His<br>CAC ]<br>CAA ] Gln<br>CAG ] | CGU ]<br>CGC ] Arg<br>CGA ]<br>CGG ] | U<br>C<br>A<br>G |
| A | AUU ]<br>AUC ] Ile<br>AUA ]<br>AUG Met | ACU ]<br>ACC ] Thr<br>ACA ]<br>ACG ] | AAU ] Asn<br>AAC ]<br>AAA ] Lys<br>AAG ] | AGU ] Ser<br>AGC ]<br>AGA ] Arg<br>AGG ] | U<br>C<br>A<br>G |
| G | GUU ]<br>GUC ] Val<br>GUA ]<br>GUG ] | GCU ]<br>GCC ] Ala<br>GCA ]<br>GCG ] | GAU ] Asp<br>GAC ]<br>GAA ] Glu<br>GAG ] | GGU ]<br>GGC ] Gly<br>GGA ]<br>GGG ] | U<br>C<br>A<br>G |

First Position (left) / Third Position (right)

It should be understood that process steps within the following description of the method may be modified changed and/or eliminated, depending on the particular preferences of the processor and/or the particular mechanical apparatus available to the processor, as well as the specific reagents and/or materials available and/or convenience and/or economics of use.

Example 1

General Materials and Methods

The present example describes some of the general techniques used in the preparation and purification of the human pro-insulin product and in the further processing of the pro-insulin into a human insulin product.

A general outline of one method, by way of example and not exclusion, to isolate and/or enrich recombinant insulin from a composition that is not enriched for recombinant insulin and/or includes pro-insulin can be described by the following series of steps:

1. Fermentation of *E. coli* transformed with the vector containing the human pro-insulin derivative-encoding amino acid sequence:
2. Lysis—Lyse the *E. coli* cells containing inclusion bodies enriched with the desired peptide, resuspended in a basic Tris/salt buffer, using a Niro Soavi homogenizer.
3. Inclusion Body Washing—Contaminant protein removal is then accomplished via two sequential washes with a Tris/Triton X-100 buffer, followed by two sequential washes with a Tris/Tween-20 buffer, and finally a single wash with a Tris/NaCl buffer.
4. Solubilization—Inclusion bodies are then solubilized in 8M urea containing reducing agents. Complete solubilization is achieved by adjusting the pH to 10.5 with NaOH.
5. Dilution refolding—The solubilized protein is then diluted into refolding buffer (5 mM CAPS, pH 10.5 at 4° C.) to a final concentration of 0.5 mg/ml. Allow the sample to refold for ≧48 hours at 2-10° C. Add an equal amount of oxidized glutathione to the initial amount of reducing agent used in the solubilization buffer, followed by 5M NaCl and 1M Phosphate additions, to final concentrations of 250 mM and 25 mM respectively. Adjust pH to 7.9 with 6M HCl.
6. IMAC Chromatography—Load the dilute pro-insulin derivative containing composition onto an IMAC column to a maximum capacity of ≦15 mg/ml of resin. Elute the pro-insulin via a 15 CV gradient from 0-400 mM Imidizole. Using RP-HPLC for analysis pool the appropriate fractions containing the Pro-Insulin peak of interest at the desired purity level.
7. Buffer exchange—To the pool, add EDTA to a final concentration of 10 mM. Exchange the buffer using a membrane with a suitable molecular weight cutoff (ex. 3000 Da). The final buffer should be at least 97% exchanged to a 20 mM Tris-Cl, pH 8.0 at 2-10° C. A protein concentration of approximately 10 mg/ml is desirable. Just prior to tryptic digest, 1M Glycine stock (pH 9.3-9.7 cold) is added to a final concentration of 100 mM and the sample pH is adjusted to 9.7 (cold).
8. Initial Trypsin Enzymatic Transformation/Proteolysis—The buffer exchanged sample is digested with a 2000:1 mass ratio of protein to trypsin. Once complete, based on HPLC, the digest is then quenched by the addition of acetic acid to ≧700 mM, to a pH of approximately 3.5. HPLC of the digest should show about 54% R30 and DI-R (30&31) insulin analogs.
9. Reverse Phase Chromatography—The digested insulin is loaded onto a C18 column and eluted isocratically using a buffer of 23% acetonitrile, 200 mM Sodium Sulfate and 0.16% phosphoric acid. Alternatively, a C4 column may be used with a 22% acetonitrile, 200 mM Sodium sulfate and 0.16% phosphoric acid buffer.
10. Buffer Exchange—Exchange the buffer using a membrane with a suitable molecular weight cutoff (3000 Da). The final buffer should be at least 97% exchanged to 5 mM acetic acid. 1M Glycine stock (pH 9.3-9.7 cold) is then added to a final concentration of 100 mM, which shifts the pH of the sample to approximately 8.6. The pH is then adjusted to approximately 9.3 with NaOH, and the sample is concentrated to 8-12 mg/ml.
11. Carboxypeptidase B transformation—The buffer exchanged sample is digested with a 1:1000 ratio of protein to carboxypeptidase B. The digest is monitored by RP-HPLC to determine reaction completion.
12. Crystallization—To the carboxypeptidase B digested insulin, an equal volume of crystallization buffer (2.4M NaCl, 0.1M Citric acid, 6 mM Zinc Chloride) is added, pH adjusted to ~6.3, and the sample is incubated at room temperature. Completion of crystallization is determined by UV analysis of the supernatant. Insulin crystals are harvested by centrifugation or filtration, washed with ethanol, and dried in vaccuo. When ready for use, the recombinant product will be solubilized and portioned into appropriate sized individually packaged units. For example, the insulin prepared according to the present invention may be prepared in 100 unit/ml vials.

Example 2

Process for Preparation of Human Pro-insulin Derivative in a Modified ptrcHis 2A (Kan) Vector The present example demonstrates one of the expression vectors that may be used in the preparation of an appropriate vector that may be used to transform an appropriate cell capable of expressing the human pro-insulin derivative. The specific vector described here is the ptrcHis2A vector. This ptrcHis2A vector was first modified before the human pro-insulin derivative-encoding nucleic acid sequence was inserted into the vector.

The ptrcHis2A vector may be purchased from a commercial vendor (e.g., Invitrogen). Such a vector will then be modified to include a Kanamycin resistance gene in the middle of the ampicillin resistance gene so as to negate the ampicillin resistance. Ampicillin resistance heightens the potential for allergic reactions to preparations made using vector constructs that include the ampicillin resistance gene. Therefore it is preferable to eliminate the ampicillin resistance in the constructs that are prepared and used.

Example 3

Construction of Purified Human ProInsulin Gene Segment for Insertion into Vector The present example is presented to demonstrate an example of the steps of a process that may be used in the present invention for preparing the human pro-insulin derivative nucleic acid sequence, as well as for preparing the modified C-peptide construct disclosed herein. The nucleic acid segment isolated in the present example was used as the starting material for creating the various insertion nucleic acid sequences described in the following examples.

The nucleic acid sequence of ATCC deposited clone, MCG-12292, was identified by the present inventors to include a nucleic acid sequence that encoded the native human pro-insulin gene. The human pro-insulin gene sequence was isolated from the nucleic acid sequence of the ATCC deposited clone, MCG-12292, and employed as a starting material in the preparation of the various modified forms of human pro-insulin and pro-insulin derivatives having the mini-C-peptide sequence substitution as defined herein.

Human Pro-insulin Gene in ATCC Clone MGC-12292: (Nucleic acid Sequence of interest=nucleic acid sequence at positions 132-392 (Pro-Insulin) of the clone). The initial pDNR-LIB vector containing the nucleic acid sequence of interest was isolated/purified from the MCG-12292 clone using a QIAprep" Spin Miniprep Kit.

The following nucleic acid sequence is a portion of the nucleic acid sequence of the ATCC Clone MGC-12292 that was identified and selected by the present inventors, and does not represent the entire nucleic acid sequence of the deposited clone.

(SEQ ID NO: 4)
```
  1 agccctccag gacaggctgc atcagaagag gccatcaagc
    agatcactgt ccttctgcca 61 tggccctgtg gatgcgcctc ctgcccctgc tggcgctgct
    ggccctctgg ggacctgacc 121 cagaggcagc ctttgtgaac caacacctgt gcggctcaca
    cctggtggaa gctctctacc 181 tagtgtgcgg ggaacgaggc ttcttctaca cacccaagac
    ccgccgggag gcagaggacc 241 tgcaggtggg gcaggtggag ctgggcgggg gccctggtgc
    aggcagcctg cagcccttgg 301 ccctggaggg gtccctgcag aagcgtggca ttgtggaaca
    atgctgtacc agcatctgct 361 ccctctacca gctggagaac tactgcaact agacgcagcc
    cgcaggcagc cccccacccg 421 ccgcctcctg caccgagaga gatggaataa agcccttgaa
    ccaacaaaaa aaaaaaaaaa 481 aaaaaaaaa aaaaa
```

The following nucleic acid sequence is a portion of the nucleic acid sequence of the ATCC Clone MGC. The portion of the nuclei acid sequence that is bolded in the above sequence represents an amino acid fragment, which is not required in the final pro-insulin molecule. The underlined portion represents the sequence fragment of interest (nucleic acids 132-392).

(SEQ ID NO: 5)
```
  1 tttgtgaac caacacctgt gcggctcaca cctggtggaa
    gctctctacc tagtgtgcgg 60
ggaacgaggc ttcttctaca cacccaagac ccgccgggag
    gcagaggacc tgcaggtggg gcaggtggag 131 ctgggcgggg gccctggtgc aggcagcctg cagcccttgg
    ccctggaggg gtccctgcag aagcgtggca 201 ttgtggaaca atgctgtacc agcatctgct ccctctacca
    gctggagaac tactgcaact ag
```

With the use of PCR, the above sequence of interest (nucleic acids 132-393) was amplified with an additional leader sequence (atgcatcatcatcatcatcatgaaggtggccgc (SEQ ID NO: 34)=new start condon, histidine tag, and tryptic cleavage sequence) and purified using a QIAprep PCR purification kit.

Translation: The amino acids below, depicts the original native as sequence coded in the ATCC Clone MGC-12292.

(SEQ ID NO: 6)
MALWMRLLPLLALLALWGPDPAAAFVNQHLCGSHLVEALYLVCERGFFY

TPKTRREAEDLQVGQVELGGGPGAGSLQPLALEGSLQKRGIVEQCCTSI

CSLYQLENYCN

The initial cloning step removed the bolded amino acid region above and replaced it with the new leader sequence in bold below. The "GGR" represents the tryptic cleavage site, which will be utilized in the tryptic transformation reaction to remove this new leader sequence.

(SEQ ID NO: 7)
MHHHHHHGGRFVNQHLCGSHLVEALYLVCERGFFYTPKT<u>RREAEDLQVGQ</u>

<u>VELGGGPGAGSLQPLALEGSLQKRG</u>IVEQCCTSICSLYQLENYCN

The underlined amino acids represent the C-peptide region of the native human pro-insulin molecule.

Cloning Procedure—

The initial cloning step into the pTrcHis2A(Kan) vector utilized the EcoR1 site for the C-terminal ligation position, and the NcoI site, indirectly, for the N-terminal ligation. In order to use an Nco 1 site directly for an N-terminal ligation, the gene of interest must contain an amino acid residue at position 2, which is encoded by a codon that starts with a guanine nucleotide. As the construct of interest does not have the required amino acid at position two, a "blunt end" ligation reaction was utilized instead of a direct NcoI "sticky end" ligation.

Sequence of the RBS site and the MCS of the ptrcHis2A (Kan) vector:

```
                                                        (SEQ ID NO: 8)
   RBS           Nco1              MCS         EcoRI
3' TAAGGAGGAATAAACCATGGATCCGAGCTCGAGATCTGCAGCTGGTACCATATGGGAATTC 5'
```

Primer Design:

Forward Primer:

The forward primer will introduce the new N-terminal Histidine Tag and tryptic cleavage site. The forward primer was ordered with a phosphorylated 5' end, which is required for the blunt end ligation reaction.

```
                                             (SEQ ID NO: 9)
5' (Phosphorylated) catcatcatcatcatcat ggtggccgc
tttgtgaaccaacacctgtgcggctc 3'
```

Reverse Primer:

The reverse primer will introduce the EcoR1 site into the C-terminus of the sequence. The EcoRI site will be used to accommodate the insertion of the Pro-insulin sequence into the vector.

```
                                            (SEQ ID NO: 10)
                                             EcoRI
    3' gatggtcgacctcttgatgacgttgatc - cttaagg 5'
```

New Generated PCR Product:

```
                                            (SEQ ID NO: 11)
          His Tag           G    G   R
5' Phos-catcatcatcatcatcatg gtggccgctt tgtgaaccaa cacctgtgcg gctcacacct ggtggaagct ctctacctag tgtgcgggga acgggcttc ttctacacac ccaagacccg ccgggaggca gaggacctgc aggtggggca ggtggagctg ggcggggcc ctggtgcagg cagcctgcag cccttggccc tggaggggtc cctgcagaag cgtggcattg tggaacaatg ctgtaccagc atctgctccc tctaccagct ggagaactac tgcaactagt cottaagg 3'
                 EcoRI
```

Following the PCR reaction, the insert DNA was purified using the QIAprep Spin Miniprep Kit from Quaigen. This purified insert DNA was used to create a pTrcHis2A(Kan) vector having this purified Pro-insulin gene sequence (See Example 4).

Example 4

Ligation Reaction for Cloning the N-Terminal Modified Pro-Insulin Gene Into the Modified pTrcHis2A (Kan) Vector The present example demonstrates the process by which the Pro-insulin gene was ligated into the modified pTrcHis2A (Kan) vector.

A 5' blunt end and a 3' EcoR1 ligation reaction were utilized to insert the Pro-insulin gene into the pTrcHis2A (Kan) vector.

Sequence at the MCS Site of the pTrcHis2A(Kan):

```
                                            (SEQ ID NO: 12)
     RBS Site       Nco1
5' TAAGGAGGAATAAACCATGGATCCGAGCTCGAGATCTGCAGCTGGTA

CCATATATGGGAATTC 3'
```

Initial Cut of the Vector with NcoI (SEQ ID NOS 13-16 Respectively in Order of Appearance):

```
5' TAAGGAGGAATAAAC 3'       NcoI cut leaves a "CATG"
                            5' overhang.

3' ATTCCTCCTTATTTGCTAC 5'

5' TAAGGAGGAATAAACCATG 3'   T4 DNA polymerase fills
                            in the opposing strand 3' ATTCCTCCTTATTTGGTAC 5'   leaving a blunt end.
```

Blunt End Reaction:

The DNA was digested with NcoI for 1 hour at 37° C. using 2 μg of DNA and 10 unites of NcoI. Following the hour digestion, 2 units of T4 DNA polymerase were added to the reaction and incubated at 12° C. for 15 minutes. The blunt end reaction was then stopped by addition of EDTA to a concentration of 10 mM and heating to 75° C. for 20 minutes. The vector DNA was then purified using the QIAprep Spin Miniprep Kit from Qiagen.

Following purification, the other end of the MCS was cut with EcoRI:

```
5' TAAGGAGGAATAAACCATG      AATTC 3'   (SEQ ID NO: 17)

3' ATTCCTCCTTATTTGGTACTTAA      G 5'   (SEQ ID NO: 18)
```

Now that the vector was prepared, the insert was digested with EcoR1, leaving a blunt ended phosphorylated N-terminus and an EcoR1 sticky end on the C-terminus. Following the EcoR1 digestions, the vector and insert DNA were both purified using the QIAprep Spin MiniPrep Kit from Qiagen.

Once purified, the insert was ligated into the vector using a 4 to 1 molar ratio of insert to vector DNA at 12° C. overnight.

Transformation

One microliter of the ligation reaction was used to transform competent BL21 *E. coli* cells, which were plated on LB-Kan agar plates and incubated overnight at 37° C. Several clones were picked and sent to IUPUI for DNA sequencing. Clones with the correct sequence were the screened for expression. Good expression was verified in all clones.

Example 5

Site Directed Mutagenesis for the Conversion of Lysine 64 to Alanine in the C-Peptide Region of Human Pro-Insulin A site directed mutageneis PCR reaction was employed to convert the lysine at position 64 to alanine. Therefore, the gene constructed in Example 4 was used as template.

The creation of this amino acid mutation eliminates the possibility of generation Arg-A0-insulin during purification. Trypsin is an enzyme that has specific cleavage activity at the C-terminus of arginine residues, and to a lesser extent, towards the C-terminus of lysine residues. In the transformation reaction, it is required that the C-peptide, including the arginine at position 65, be removed along with the N-terminal sequence. If trypsin cleaves at the lysine in position 64, it will be unable to remove the arginine at position 65, due the fact that it requires at least one residue on both sides of a cleavage site. What results is the production of an unwanted by-product, arg-A-0-insulin. This by-product constitutes a small loss in yield and generates an undesired contaminant.

By converting this lysine 65 into another uncharged amino acid, particularly alanine, the arg-AO-insulin product is not formed. This is because the trypsin no longer acts to cleave at this particular site of the pro-insulin sequence.

Site directed mutagenensis was used to convert the lysine at position 64 to alanine. The procedure was adapted from the protocol in the Stratagene Quick Change Site Directed Mutagenesis kit. The PCR reaction utilized pFU Turbo polymerase because of its high fidelity compared with Taq polymerase. Site directed mutagenesis involves the synthesis of the entire gene along with the vector (pTrcHis2A(Kan)). The insulin (Met-His-tagged-Gly-Gly-Arg)/)pTrcHis2A(Kan) clone synthesized above (Example 4) was used as the template for the PCR reaction.

PCR Primers Used:

```
                                          (SEQ ID NO: 19)
Initial sequence
                K64
5' ccctggaggggtccctgcagaagcgtggcattgtggaacaatgctgt
acc 3'

Forward Primer                            (SEQ ID NO: 20)
5' ggggtccctgcaggcgcgtggcattgtg 3'

Reverse Primer                            (SEQ ID NO: 21)
3' ccccagggacgtccgcgcaccgtaacac 5'
```

The 50 µl PCR reaction was treated with 20 units of Dpnl, and incubated at 37° C. for 1 hour to digest all methylated template DNA before transforming chemically competent BL21 cells.

Following transformation into BL21 cells, several clones were sequenced for gene verification. The clone that was isolated was:

Met-His-taggedGly-Gly-Arg/Pro-insulin/K64A/pTrcHis2A(Kan).

The expression of this clone was very good.

Final Gene product (Met-His tagged/Gly-Gly-Arg/Pro-insulin/K64A):

```
                                          (SEQ ID NO: 22)
5' ATGCATCATCATCATCATCATGGTGGCCGCTTTGTGAACCAACACCT

GTGCGGCTCACACCTGGTGGAAGCTCTCTACCTAGTGTGCGGGGAACGAG

GCTTCTTCTACACACCCAAGACCCGCCGGGAGGCAGAGGACCTGCAGGTG

GGGCAGGTGGAGCTGGGCGGGGGCCCTGGTGCAGGCAGCCTGCAGCCCTT

GGCCCTGGAGGGGTCTCTGCAGGCGCGTGGCATTGTGGAACAATGCTGTA

CCAGCATCTGCTCCCTCTACCAGCTGGAGAACTACTGCAACTAG3'
```

Amino Acid Sequence of the His-tagged/Gly-Gly-Arg/K64A Pro-insulin:

```
                                          (SEQ ID NO: 23)
MHHHHHHGGRFVNQHLCGSHLVEALYLVCGERGFFYTPKTRREAEDLQVG

QVELGGGPGAGSLQPLALEGSLQARGIVEQCCISICSLYQLENYCN
```

In the nucleic acid and amino acid sequences above, the bold and underlined portions identifies the connecting C-peptide sequence.

Example 6

Full Length Substituted Pro-Insulin Construct and Uses Thereof in Production of Human Insulin With regards to the full length Pro-Insulin substitution construct of His-Tagged/K64A, three unique modifications are present to the original gene that simplify purification and increase yield.

1) The N-terminal sequence was modified by the addition of a 6-Histadine tag (SEQ ID NO: 24, which could be used to simplify the purification via the use of a Nickel chelating column as an initial purification step following refolding.

2) Following the 6-His tag (SEQ ID NO: 24) sequence on the N-terminus, a well documented tryptic cleavage site was introduced in order to provide a simple means of removing the N terminal tag following the metal chelating chromatography step. The sequence introduced was "Glycine, Glycine, Arginine", with cleavage after the arginine.

3) The third modification was the conversion of an amino acid located at position 64 (original Pro-insulin) of the native sequence, which is a lysine residue that is converted to alanine. The modification prevents the formation of arg-AO-insulin during the tryptic cleavage transformation step, which increases the theoretical yield.

All data thus far supports the modifications. The initial chelating column step yields a Tagged-Pro-Insulin pool of approximately greater than or equal to about 92% purity. The tryptic transformation step yields a final insulin molecule with high digestion efficiency which demonstrates the effectiveness of the "gly, gly, arg" cleavage sequence for N-terminal removal and the lack of an Arg-A-0-insulin at position 65 demonstrate the advantage of the replacement at position 64.

The individual transformation reactions, rather then a single transformation reaction, allows for the efficient removal of the Desthreonine byproduct which is created by cleavage at the Lysine at position 29. This cleavage can be minimized in the native sequence by introducing nickel to the transformation reactions. However, the presence of the Histidine tag in the clone described herein, prevents this nickel protection of lysine 29. The separate transformation reactions allows for almost complete removal of the desthreonine byproduct, which is created when trypsin cleaves at the lysine at position 28, removing the threonine at position 29.

Figure 2A:
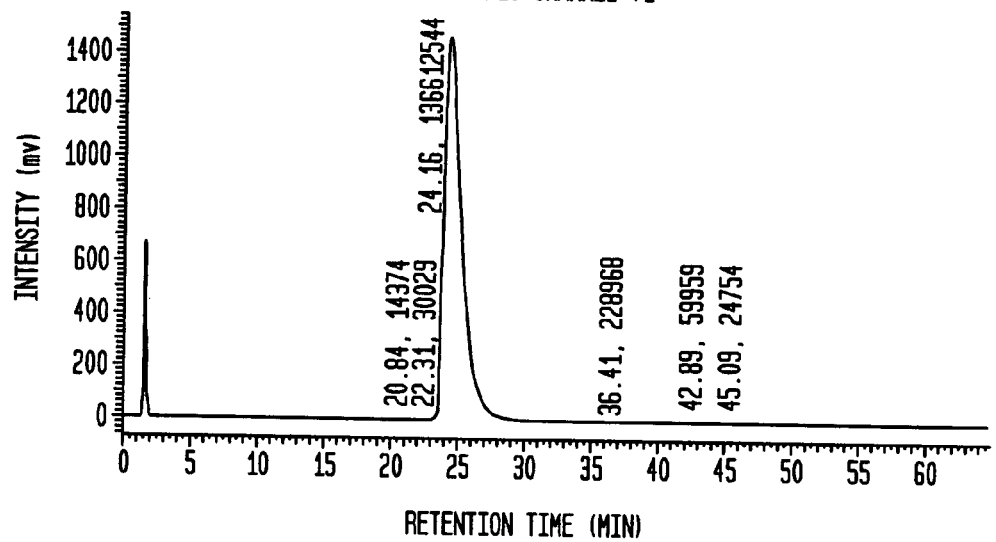
FIG. 2, according to one aspect of the invention, presents an HPLC of recombinant IPT human insulin. The chromatograph demonstrates that the preparation is high in purity with almost non-existent levels of pro-insulin.
Figure 2B:
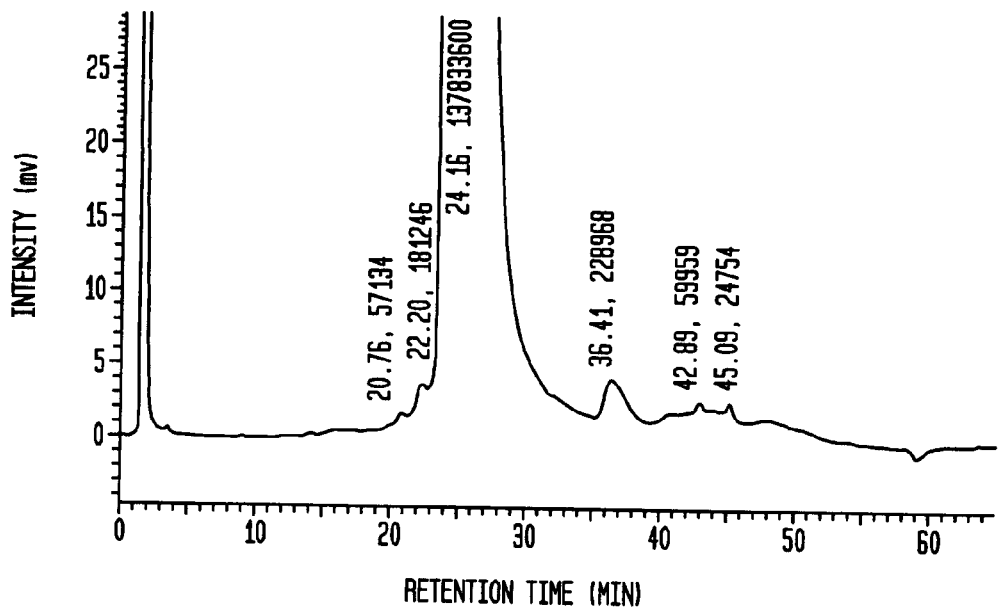

The final purification steps, including the Reverse phase Chromatography, carboxy peptidase B transformation reactions and crystallization, yields a highly pure insulin (≧99%) sample, which by HPLC reverse phase analysis shows essentially no Pro-insulin analogs or N-terminal fragments (See FIG. 2). As well, the desthreonine contaminant can essentially be completely removed.

Amino Acid Sequence:

(SEQ ID NO: 25)
Natural Pro-Insulin Amino Acid Sequence:
MALWMRLLPLLALLALWGPDPAAAFVNQHLCGSHLVEALYLVCGERGFF

YTPKTRREAEDLQVGQVELGGGPGAGSLQPLALEGSLQKRGIVEQCCTS

ICSLYQLENYCN (SEQ ID NO: 26)
Replacement of initial sequence with Tag and
cleavage site:
MHHHHHHGGRFVNQHLCGSHLVEALYLVCGERGFFYTPKTRREAEDLQVG

QVELGGGPGAGSLQPLALEGSLQKRGIVEQCCTSICSLYQLENYCN (SEQ ID NO: 27)
Conversion of lysine 64 to alanine:
MHHHHHHGGRFVNQHLCGSHLVEALYLVCGERGFFYTPKTRREAEDLQVG

QVELGGGPGAGSLQPLALEGSLQARGIVEQCCTSICSLYQLENYCN

Example 7

Biopotency Study of the Full Length Substituted Pro-Insulin Construct

The final purified Insulin samples were tested in vivo on rabbits to compare the biopotency against Humulin R. As analytical studies give a simple picture of a biological molecules relative state compared with a standard, it is imperative that a bioassay be used to determine that the purified molecule of interest carries the required biological activity.

In Vivo Biological Method

The biological assay was based on the current accepted procedure outlined in the United States Pharmacopeia. Testing was conducted by MPI Research.

Test subjects included 30 male rabbits which were giving injections on two separate days of either, the control (saline), positive control (Humulin R), or test sample (IPT (Elona Biotechnologies) Human insulin), through subcutaneous injection.

Dosing levels consisted of 0.35 or 0.7 international units (IU), administered at a dose volume of 0.35 ml/dose. The control group received saline on both days 1 and 3 at a dose volume of 0.35 ml/dose.

Figure 3A:
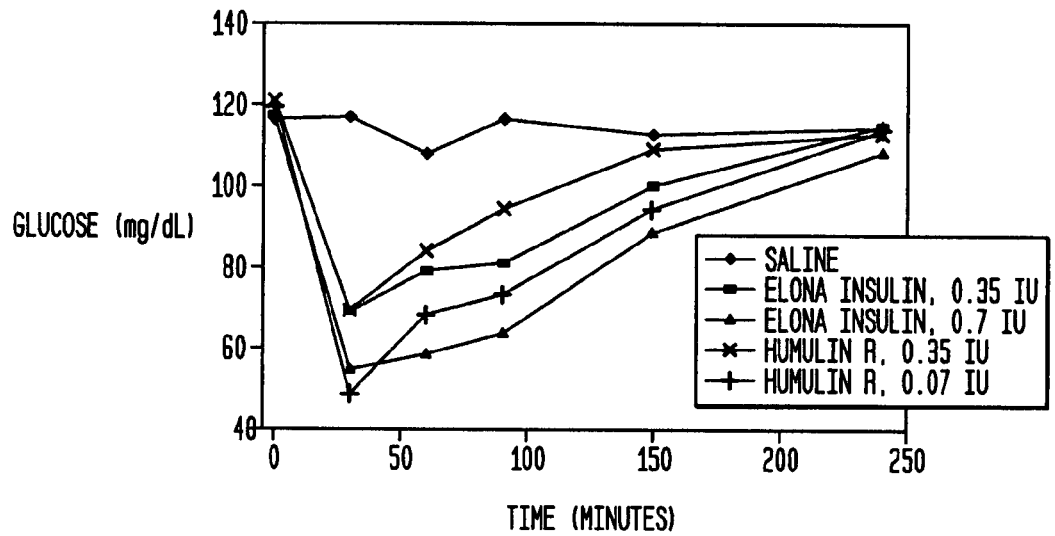
FIG. 3, according to some aspects of the invention, presents a biopotency study showing relative glucose curves for rabbits injected with saline (control), Humulin R (positive control), and Elona Biotechnologies human insulin (test sample).
Figure 3B:
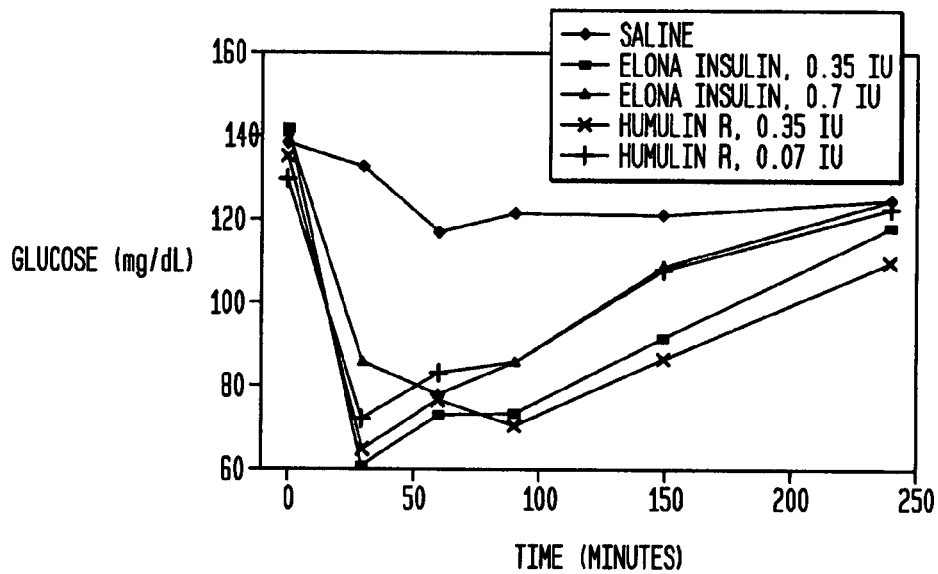
Figure 4:
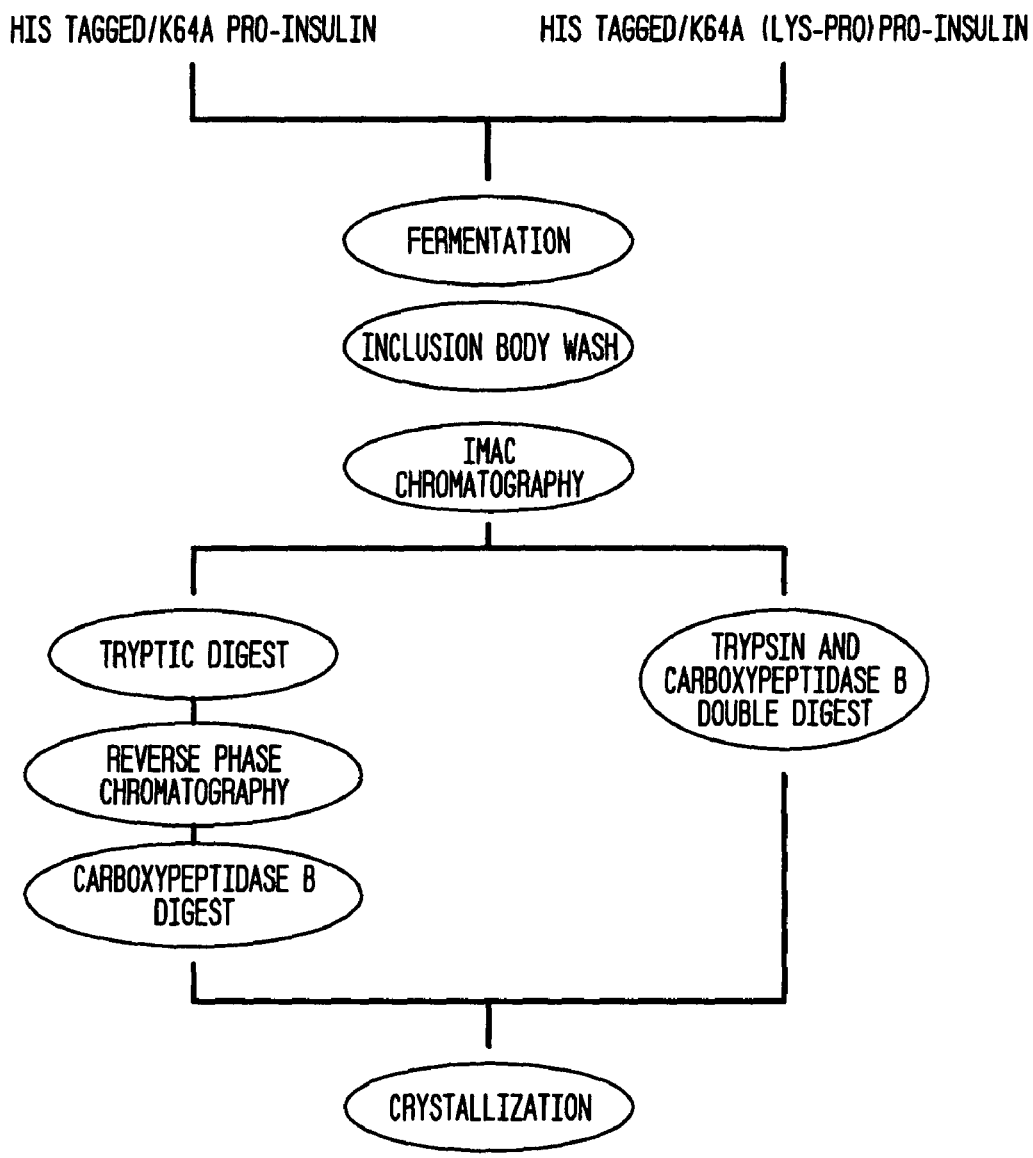
FIG. 4, according to some aspects to the invention, presents a flow scheme for the purification of insulin and Lys-Pro insulin, using the purification methods described in examples 1 and 9.

Glucose monitoring was conducted prior to dosing and at 30, 60, 90, 150, and 240 minutes following dosing on both days. Results showed comparable biopotency of IPT human insulin with Humulin R (see FIG. 3).

Example 8

Pro-Insulin Constructs

The present example demonstrates the utility of the present invention for providing unique Pro-Insulin constructs that are particularly useful and efficient in the methods of insulin production described herein.

Native Pro-Insulin AA sequene:

(SEQ ID NO: 28)
FVNQHLCGSHLVEALYLVCGERGFFYTPKTRREAEDLQVGQVELGGGPGA

GSLQPLALEGSLQKRGIVEQCCTSICSLYQLENYCN

N-terminal 6-His tagged (SEQ ID NO: 24) clone with tryptic cleavage sequence for removal: (Utilization of a Nickel chelating column for high purity in a single step)

(SEQ ID NO: 29)
MHHHHHHGGRFVNQHLCGSHLVEALYLVCGERGFFYTPKTRREAEDLQVG

QVELGGGPGAGSLQPLALEGSLQKRGIVEQCCTSICSLYQLENYCN

Site Directed Mutagenesis of Lysine 64 to Alanine:
Prevention of incorrect cleavage following the lysine. No arg-insulin contaminant generated, resulting in an increased yield.

(SEQ ID NO: 30)
MHHHHHHGGRFVNQHLCGSHLVEALYLVCGERGFFYTPKTRREAEDLQVG

QVELGGGPGAGSLQPLALEGSLQ<u>A</u>RGIVEQCCTSICSLYQLENYCN

Example 9

Purification Method for Production of Lys/Pro Insulin

The present example demonstrates the utility of the present invention for providing a unique construct and purification scheme that significantly improves the purification method for the production of Lys/Pro Insulin.

Lys/Pro Insulin is characterized as a short acting insulin analog, which, when combined with am insulin pump, allows for better blood glucose stability without the risk of hyperglycemia.

Amino acid sequence of the unique construct as defined in example 8.

(SEQ ID NO: 30)
MHHHHHHGGRFVNQHLCGSHLVEALYLVCGERGFFYTPKTRREAEDLQVG

QVELGGGPGAGSLQPLALEGSLQ<u>A</u>RGIVEQCCTSICSLYQLENYCN

Lys/Pro insulin modification with residues 28 and 29 reversed in their order:

(SEQ ID NO: 31)
MHHHHHHGGRFVNQHLCGSHLVEALYLVCGERGFFYT<u>KP</u>TRREAEDLQVG

QVELGGGPGAGSLQPLALEGSLQARGIVEQCCTSICSLYQLENYCN

A general outline of one method, by way of example and not exclusion, to isolate and/or enrich recombinant Lys/Pro insulin from a composition that is not enriched for recombinant Lys/Pro insulin and/or includes pro-insulin can be described by the following series of steps:

1. Fermentation of *E. coli* transformed with the vector containing the human pro-insulin derivative-encoding amino acid sequence:
2. Lysis—Lyse the *E. coli* cells containing inclusion bodies enriched with the desired peptide, resuspended in a basic Tris/salt buffer, using a Niro Soavi homogenizer.
3. Inclusion Body Washing—Contaminant protein removal is then accomplished via two sequential washes with a Tris/Triton X-100 buffer, followed by two sequential washes with a Tris/Tween-20 buffer, and finally a single wash with a Tris/NaCl buffer.
4. Solubilization—Inclusion bodies are then solubilized in 8M urea containing reducing agents. Complete solubilization is achieved by adjusting the pH to 10.5 with NaOH.
5. Dilution refolding—The solubilized protein is then diluted into refolding buffer (5 mM CAPS, pH 10.5 at 4° C.) to a final concentration of 0.5 mg/ml. Allow the sample to refold for ≧48 hours at 2-10° C. Add an equal amount of oxidized glutathione to the initial amount of reducing agent used in the solubilization buffer, followed by 5M NaCl and 1M Phosphate additions, to final concentrations of 250 mM and 25 mM respectively. Adjust pH to 7.9 with 6M HCl.
6. IMAC Chromatography—Load the dilute pro-insulin derivative containing composition onto an IMAC column to a maximum capacity of ≦15 mg/ml of resin. Elute the pro-insulin via a 15 CV gradient from 0-400 mM Imidizole. Using RP-HPLC for analysis, pool the appropriate fractions containing the Pro-Insulin peak of interest at the desired purity level.
7. Buffer exchange—To the pool, add EDTA to a final concentration of 10 mM. Exchange the buffer using a membrane with a suitable molecular weight cutoff (ex. 3000 Da). The final buffer should be at least 97% exchanged to a 20 mM Tris-Cl, pH 8.0 at 2-10° C. A protein concentration of approximately 20-25 mg/ml is desirable.
8. Trypsin and Carboxypeptidase Enzymatic Transformation—The buffer exchanged sample is digested with a 2000:1 and 1000:1 mass ratio of protein to trypsin and protein to carboxypeptidase B respectively. Once complete, based on HPLC, the digest is then quenched by the addition of acetic acid to ≧700 mM, to a pH of approximately 3.5. HPLC of the digest should show about 54% Humalog (Lys/Pro insulin).
9. Reverse Phase Chromatography—The digested Lys/Pro insulin is loaded onto a C18 column and eluted isocratically using a buffer of 23% acetonitrile, 200 mM Sodium Sulfate and 0.16% phosphoric acid. Alternatively, a C4 column may be used with a 22% acetonitrile, 200 mM Sodium sulfate and 0.16% phosphoric acid buffer.
10. Buffer Exchange—Exchange the buffer using a membrane with a suitable molecular weight cutoff (~3000 Da). The final buffer should be at least 97% exchanged to 0.01N acid, and the sample is concentrated to 8-12 mg/ml.
11. Crystallization—To the Lys/Pro insulin, an equal volume of crystallization buffer (2.4M NaCl, 0.1M Citric acid, 6 mM Zinc Chloride) is added, pH adjusted to ~6.3, and the sample is incubated at room temperature. Completion of crystallization is determined by UV analysis of the supernatant. Insulin crystals are harvested by centrifugation or filtration, washed with ethanol, and dried in vaccuo. When ready for use, the recombinant product will be solubilized and portioned into appropriate sized individually packaged units. For example, the insulin prepared according to the present invention may be prepared in 100 unit/ml vials.

The present example demonstrates several advantages that utilization of the Lys/pro insulin construct has over the original insulin sequence used in the purification scheme seen Example 1:

a. Step 7 does not require the Glycine addition and pH adjustment to 9.7, which decreases the chances of desamino formation, typically seen in the high or low pH ranges.
b. The separate digestion reaction found in steps 8 and 11 of Example 1 are combined into a single digestion reaction in Step 8 above, which is carried out at pH 8.0, which decreases the possibility of desamino formation.
c. The Lys/pro insulin construct prevents the formation of Desthreonine-insulin, which is created in the trypsin transformation reaction. It represents approximately a 6-10% yield loss, and can only be separated from the Arg and Di-Arg insulin species on the reverse phase step.

Example 10

Sodium Sulfate in Recovery Process for Insulin

The reverse phase chromatography step for purification of Di-Arg and Single-Arg insulin species following tryptic digestion and prior to carboxypeptidase B digestion involves one of two methods:

1. A shallow gradient elution from 23.5% to 25% acetonitrile in the presence of 200 mM sodium sulfate and 0.16% phosphate, over 15 column volumes.
2. An isocratic elution of 23.5% acetonitrile in the presence of 200 mM sodium sulfate and 0.16% phosphate, over approximately 15 column volumes.

The above methods are specific to a C18 reverse phase system with a 15 μM particle size and 200-300 Å pore, but may be adapted to a C4 or C8 system by adjusting the acetonitrile concentrations. As well, the particle size may be varied to decrease back pressure.

Figure 5A:
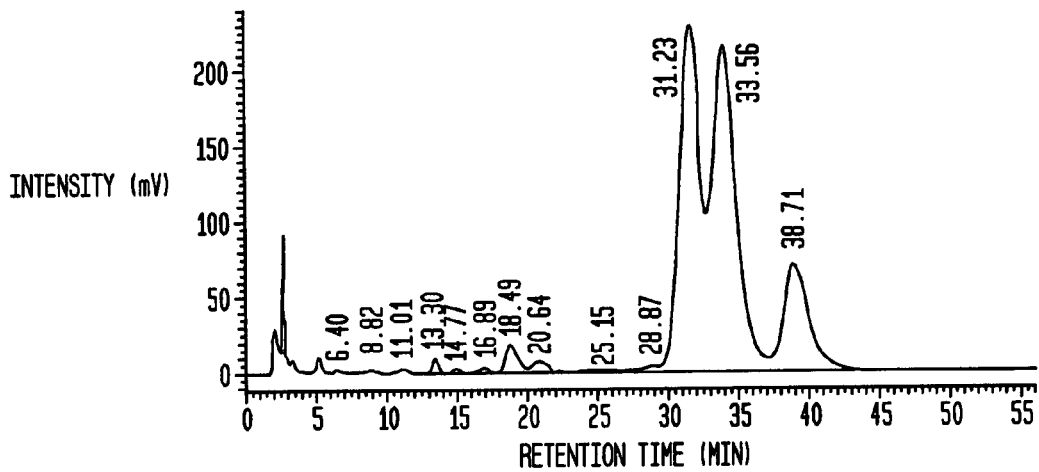
FIGS. 5A and 5B, according to some aspects of the invention, presents a reverse phase chromatography analysis of chromatogram with (5A) and without (5B) sodium sulfate.
Figure 5B:
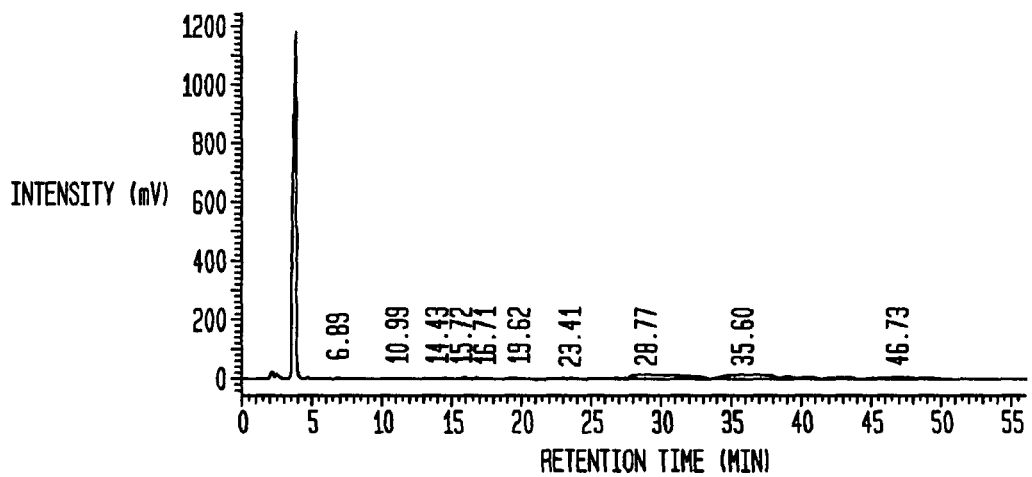

A study of the above methods was conducted to look at the effects of sodium sulfate on the chromatography. It was found that the sodium sulfate when removed from the buffers resulted in a high yield loss. The material did not seem to stick to the column effectively, leading to some material crashing off at the column void volume. Sodium sulfate is required to increase mass transfer within the column. (See FIGS. 5A and 5B).

This study demonstrates the requirement of sodium sulfate in the reverse phase buffers. Although a more detailed study has not been conducted to determine the minimum required concentration, it is also understood that the flow rate during loading is a crucial parameter, since the slower the load, the better chance that there will be binding to the column before the void volume is through.

All of the compositions and methods disclosed and claimed herein can be made and expressed without undue experimentation in light of the present disclosure.

While the compositions and methods of this invention have been described in terms of preferred embodiments, it will be apparent to those of skill in the art that variations may be applied to the compositions, the methods, and in the steps and in the sequence of steps of the methods and processes described herein without departing from the concept, spirit and scope of the invention. More specifically, it will be apparent that certain agents which are both chemically and physiologically related may be substituted for the agents described herein while the same or similar results would be achieved.

All such similar substitutions and modifications apparent to those skilled in the art are deemed to be within the spirit, scope and concept of the inventions disclosed herein by the appended claims. Accordingly, the exclusive rights sought to be patented are as described in the claims below.

BIBLIOGRAPHY

The following references are specifically incorporated in their entirety.
1. U.S. Pat. No. 6,777,207 B2—Kjeldsen et al. (2004).
2. U.S. Pat. No. 4,916,212—Markussen et al. (1990).
3. U.S. Pat. No. 5,962,267—Shin et al. (1999).
4. EP Patent No. 0 055 945—Goeddel et al. (1981).
5. Chance et al. (1981), Peptides: Proceedings of the 7$^{th}$ American Peptide Chemistry Symposium, pp. 721-728 (Rich, D. and Gross, E. eds.).
6. Chan et al. (1981), P.N.A.S., U.S.A., 78:5401-5404.
7. Thim et al. (1986), P.N.A.S., U.S.A., 83: 6766-6770.
8. Frank et al. (1981), Peptides: Proceedings of the 7$^{th}$ American Peptide Chemistry Symposium, pp. 729-739 (Rich, D. and Gross, E. eds.).
9. Chang et al. (1998), Bio hern J. 329:631-635.

What is claimed is:

1. A composition comprising a peptide comprising:

B chain—RREAEALQVGQVELGGGPGAGSLQPLA-LEGSLQAR (SEQ ID NO: 32)—

A chain, wherein said A chain and said B chain are native human insulin chains.

2. The composition of claim 1 wherein the peptide further comprising a His-tag at the N-terminus of the B-chain.

3. The composition of claim 2 wherein the His-tag comprises SEQ ID NO: 2.

4. A pharmaceutical product comprising a composition as defined in claim 1 and a pharmaceutically acceptable carrier solution.

* * * * *

SEQUENCE LISTING

```
<160> NUMBER OF SEQ ID NOS: 35

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Pro Gly Asp Val
 1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met His His His His His His Gly Gly Arg
 1               5                  10

<210> SEQ ID NO 3
<211> LENGTH: 51
<212> TYPE: PRT
<213> ORGANISM: Homo sapiens

<400> SEQUENCE: 3

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr Gly Ile
            20                  25                  30

Val Glu Gln Cys Cys Thr Ser Ile Cys Ser Leu Tyr Gln Leu Glu Asn
        35                  40                  45

Tyr Cys Asn
    50

<210> SEQ ID NO 4
<211> LENGTH: 495
<212> TYPE: DNA
<213> ORGANISM: Artificial Sequence
<220> FEATURE:
<223> OTHER INFORMATION: Description of Artificial Sequence: Synthetic
      nucleotide construct
```

```
<400> SEQUENCE: 4
agccctccag gacaggctgc atcagaagag gccatcaagc agatcactgt ccttctgcca        60
tggccctgtg gatgcgcctc ctgcccctgc tggcgctgct ggccctctgg ggacctgacc       120
cagaggcagc ctttgtgaac caacacctgt gcggctcaca cctggtggaa gctctctacc       180
tagtgtgcgg ggaacgaggc ttcttctaca cacccaagac ccgccgggag cagaggacc       240 tgcaggtggg gcaggtggag ctgggcgggg gccctggtgc aggcagcctg cagcccttgg       300
ccctggaggg gtccctgcag aagcgtggca ttgtggaaca atgctgtacc agcatctgct       360
ccctctacca gctggagaac tactgcaact agacgcagcc cgcaggcagc ccccacccg        420 ccgcctcctg caccgagaga gatggaataa agcccttgaa ccaacaaaaa aaaaaaaaa       480 aaaaaaaaaa aaaaa                                                       495

<210> SEQ ID NO 5
<211> LENGTH: 261
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 5
tttgtgaacc aacacctgtg cggctcacac ctggtggaag ctctctacct agtgtgcggg        60
gaacgaggct tcttctacac acccaagacc cgccgggagg cagaggacct gcaggtgggg       120
caggtggagc tgggcggggg ccctggtgca ggcagcctgc agcccttggc cctggagggg       180
tccctgcaga agcgtggcat tgtggaacaa tgctgtacca gcatctgctc cctctaccag       240
ctggagaact actgcaacta g                                                 261

<210> SEQ ID NO 6
<211> LENGTH: 109
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 6

Met Ala Leu Trp Met Arg Leu Leu Pro Leu Leu Ala Leu Leu Ala Leu
  1               5                  10                  15

Trp Gly Pro Asp Pro Ala Ala Ala Phe Val Asn Gln His Leu Cys Gly
                 20                  25                  30

Ser His Leu Val Glu Ala Leu Tyr Leu Val Cys Glu Arg Gly Phe Phe
             35                  40                  45

Tyr Thr Pro Lys Thr Arg Arg Glu Ala Glu Asp Leu Gln Val Gly Gln
         50                  55                  60

Val Glu Leu Gly Gly Gly Pro Gly Ala Gly Ser Leu Gln Pro Leu Ala
 65                  70                  75                  80

Leu Glu Gly Ser Leu Gln Lys Arg Gly Ile Val Glu Gln Cys Cys Thr
                 85                  90                  95

Ser Ile Cys Ser Leu Tyr Gln Leu Glu Asn Tyr Cys Asn
            100                 105

<210> SEQ ID NO 7
<211> LENGTH: 95
<212> TYPE: PRT
<213> ORGANISM: Artificial Sequence
```

```
<220> FEATURE:
<223> OTHER INFORMATION: Description of Artificial Sequence: Synthetic
      peptide construct

<400> SEQUENCE: 7

Met His His His His His Gly Gly Arg Phe Val Asn Gln His Leu
1               5                   10                  15

Cys Gly Ser His Leu Val Glu Ala Leu Tyr Leu Val Cys Glu Arg Gly
                20                  25                  30

Phe Phe Tyr Thr Pro Lys Thr Arg Glu Ala Glu Asp Leu Gln Val
            35                  40                  45

Gly Gln Val Glu Leu Gly Gly Pro Gly Ala Gly Ser Leu Gln Pro
    50                  55                  60

Leu Ala Leu Glu Gly Ser Leu Gln Lys Arg Gly Ile Val Glu Gln Cys
65                  70                  75                  80

Cys Thr Ser Ile Cys Ser Leu Tyr Gln Leu Glu Asn Tyr Cys Asn
                85                  90                  95

<210> SEQ ID NO 8
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cttaagggta taccatggtc gacgtctaga gctcgagcct aggtaccaaa taaggaggaa    60
t                                                                   61

<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: n-term phosphorylated

<400> SEQUENCE: 9
catcatcatc atcatcatgg tggccgcttt gtgaaccaac acctgtgcgg ctc           53

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggaattccta gttgcagtag ttctccagct ggtag                              35

<210> SEQ ID NO 11
<211> LENGTH: 296
<212> TYPE: DNA
<213> ORGANISM: Artificial Sequence
<220> FEATURE:
<223> OTHER INFORMATION: Description of Artificial Sequence: Synthetic
      nucleotide construct
```

```
<220> FEATURE:
<221> NAME/KEY: modified_base
<222> LOCATION: (1)
<223> OTHER INFORMATION: n-term phosphorylated

<400> SEQUENCE: 11
catcatcatc atcatcatgg tggccgcttt gtgaaccaac acctgtgcgg ctcacacctg      60
gtggaagctc tctacctagt gtgcggggaa cgggcttctt ctacacaccc aagacccgcc    120
gggaggcaga ggacctgcag gtggggcagg tggagctggg cggggccct ggtgcaggca     180 gcctgcagcc cttggccctg gaggggtccc tgcagaagcg tggcattgtg gaacaatgct    240
gtaccagcat ctgctccctc taccagctgg agaactactg caactagtcc ttaagg        296

<210> SEQ ID NO 12
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
taaggaggaa taaaccatgg atccgagctc gagatctgca gctggtacca tatatgggaa     60
ttc                                                                   63

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
taaggaggaa taaac                                                      15

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
catcgtttat tcctcctta                                                  19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
taaggaggaa taaaccatg                                                  19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 16
catggtttat tcctcctta                                                19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
taaggaggaa taaaccatg                                                19

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aattcatggt ttattcctcc tta                                           23

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccctggaggg gtccctgcag aagcgtggca ttgtggaaca atgctgtacc              50

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggggtccctg caggcgcgtg gcattgtg                                      28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cacaatgcca cgcgcctgca gggacccc                                      28

<210> SEQ ID NO 22
<211> LENGTH: 291
<212> TYPE: DNA
<213> ORGANISM: Artificial Sequence
<220> FEATURE:
<223> OTHER INFORMATION: Description of Artificial Sequence: Synthetic
      nucleotide construct
```

```
<400> SEQUENCE: 22
atgcatcatc atcatcatca tggtggccgc tttgtgaacc aacacctgtg cggctcacac      60
ctggtggaag ctctctacct agtgtgcggg gaacgaggct tcttctacac acccaagacc     120
cgccgggagg cagaggacct gcaggtgggg caggtggagc tgggcggggg ccctggtgca     180
ggcagcctgc agcccttggc cctggagggg tctctgcagg cgcgtggcat tgtggaacaa     240
tgctgtacca gcatctgctc cctctaccag ctggagaact actgcaacta g              291

<210> SEQ ID NO 23
<211> LENGTH: 96
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 23

Met His His His His His His Gly Gly Arg Phe Val Asn Gln His Leu
 1               5                  10                  15

Cys Gly Ser His Leu Val Glu Ala Leu Tyr Leu Val Cys Gly Glu Arg
            20                  25                  30

Gly Phe Phe Tyr Thr Pro Lys Thr Arg Arg Glu Ala Glu Asp Leu Gln
        35                  40                  45

Val Gly Gln Val Glu Leu Gly Gly Gly Pro Gly Ala Gly Ser Leu Gln
    50                  55                  60

Pro Leu Ala Leu Glu Gly Ser Leu Gln Ala Arg Gly Ile Val Glu Gln
65                  70                  75                  80

Cys Cys Ile Ser Ile Cys Ser Leu Tyr Gln Leu Glu Asn Tyr Cys Asn
                85                  90                  95

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 24

His His His His His His
 1               5

<210> SEQ ID NO 25
<211> LENGTH: 110
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 25

Met Ala Leu Trp Met Arg Leu Leu Pro Leu Leu Ala Leu Leu Ala Leu
 1               5                  10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60
```

```
Gln Val Glu Leu Gly Gly Pro Gly Ala Gly Ser Leu Gln Pro Leu
 65                  70                  75                  80

Ala Leu Glu Gly Ser Leu Gln Lys Arg Gly Ile Val Glu Gln Cys Cys
                 85                  90                  95

Thr Ser Ile Cys Ser Leu Tyr Gln Leu Glu Asn Tyr Cys Asn
            100                 105                 110

<210> SEQ ID NO 26
<211> LENGTH: 96
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 26

Met His His His His His His Gly Gly Arg Phe Val Asn Gln His Leu
 1               5                  10                  15

Cys Gly Ser His Leu Val Glu Ala Leu Tyr Leu Val Cys Gly Glu Arg
             20                  25                  30

Gly Phe Phe Tyr Thr Pro Lys Thr Arg Arg Glu Ala Glu Asp Leu Gln
         35                  40                  45

Val Gly Gln Val Glu Leu Gly Gly Gly Pro Gly Ala Gly Ser Leu Gln
     50                  55                  60

Pro Leu Ala Leu Glu Gly Ser Leu Gln Lys Arg Gly Ile Val Glu Gln
 65                  70                  75                  80

Cys Cys Thr Ser Ile Cys Ser Leu Tyr Gln Leu Glu Asn Tyr Cys Asn
                 85                  90                  95

<210> SEQ ID NO 27
<211> LENGTH: 96
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 27

Met His His His His His His Gly Gly Arg Phe Val Asn Gln His Leu
 1               5                  10                  15

Cys Gly Ser His Leu Val Glu Ala Leu Tyr Leu Val Cys Gly Glu Arg
             20                  25                  30

Gly Phe Phe Tyr Thr Pro Lys Thr Arg Arg Glu Ala Glu Asp Leu Gln
         35                  40                  45

Val Gly Gln Val Glu Leu Gly Gly Gly Pro Gly Ala Gly Ser Leu Gln
     50                  55                  60

Pro Leu Ala Leu Glu Gly Ser Leu Gln Ala Arg Gly Ile Val Glu Gln
 65                  70                  75                  80

Cys Cys Thr Ser Ile Cys Ser Leu Tyr Gln Leu Glu Asn Tyr Cys Asn
                 85                  90                  95

<210> SEQ ID NO 28
<211> LENGTH: 86
<212> TYPE: PRT
<213> ORGANISM: Artificial Sequence
<220> FEATURE:
<223> OTHER INFORMATION: Description of Artificial Sequence: Synthetic
      peptide construct
```

-continued

```
<400> SEQUENCE: 28

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr Arg Arg
             20                  25                  30

Glu Ala Glu Asp Leu Gln Val Gly Gln Val Glu Leu Gly Gly Gly Pro
         35                  40                  45

Gly Ala Gly Ser Leu Gln Pro Leu Ala Leu Glu Gly Ser Leu Gln Lys
     50                  55                  60

Arg Gly Ile Val Glu Gln Cys Cys Thr Ser Ile Cys Ser Leu Tyr Gln
 65                  70                  75                  80

Leu Glu Asn Tyr Cys Asn
                 85

<210> SEQ ID NO 29
<211> LENGTH: 96
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 29

Met His His His His His Gly Gly Arg Phe Val Asn Gln His Leu
 1               5                  10                  15

Cys Gly Ser His Leu Val Glu Ala Leu Tyr Leu Val Cys Gly Glu Arg
             20                  25                  30

Gly Phe Phe Tyr Thr Pro Lys Thr Arg Arg Glu Ala Glu Asp Leu Gln
         35                  40                  45

Val Gly Gln Val Glu Leu Gly Gly Gly Pro Gly Ala Gly Ser Leu Gln
     50                  55                  60

Pro Leu Ala Leu Glu Gly Ser Leu Gln Lys Arg Gly Ile Val Glu Gln
 65                  70                  75                  80

Cys Cys Thr Ser Ile Cys Ser Leu Tyr Gln Leu Glu Asn Tyr Cys Asn
                 85                  90                  95

<210> SEQ ID NO 30
<211> LENGTH: 96
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 30

Met His His His His His Gly Gly Arg Phe Val Asn Gln His Leu
 1               5                  10                  15

Cys Gly Ser His Leu Val Glu Ala Leu Tyr Leu Val Cys Gly Glu Arg
             20                  25                  30

Gly Phe Phe Tyr Thr Pro Lys Thr Arg Arg Glu Ala Glu Asp Leu Gln
         35                  40                  45

Val Gly Gln Val Glu Leu Gly Gly Gly Pro Gly Ala Gly Ser Leu Gln
     50                  55                  60

Pro Leu Ala Leu Glu Gly Ser Leu Gln Ala Arg Gly Ile Val Glu Gln
 65                  70                  75                  80

Cys Cys Thr Ser Ile Cys Ser Leu Tyr Gln Leu Glu Asn Tyr Cys Asn
                 85                  90                  95
```

```
<210> SEQ ID NO 31
<211> LENGTH: 96
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 31

Met His His His His His Gly Gly Arg Phe Val Asn Gln His Leu
 1               5                  10                  15

Cys Gly Ser His Leu Val Glu Ala Leu Tyr Leu Val Cys Gly Glu Arg
                20                  25                  30

Gly Phe Phe Tyr Thr Lys Pro Thr Arg Glu Ala Glu Asp Leu Gln
            35                  40                  45

Val Gly Gln Val Glu Leu Gly Gly Pro Gly Ala Gly Ser Leu Gln
        50                  55                  60

Pro Leu Ala Leu Glu Gly Ser Leu Gln Ala Arg Gly Ile Val Glu Gln
 65                  70                  75                  80

Cys Cys Thr Ser Ile Cys Ser Leu Tyr Gln Leu Glu Asn Tyr Cys Asn
                85                  90                  95

<210> SEQ ID NO 32
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Arg Glu Ala Glu Ala Leu Gln Val Gly Gln Val Glu Leu Gly Gly
 1               5                  10                  15

Gly Pro Gly Ala Gly Ser Leu Gln Pro Leu Ala Leu Glu Gly Ser Leu
                20                  25                  30

Gln Ala Arg
        35

<210> SEQ ID NO 33
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Arg Glu Ala Glu Asp Leu Gln Val Gly Gln Val Glu Leu Gly Gly
 1               5                  10                  15

Gly Pro Gly Ala Gly Ser Leu Gln Pro Leu Ala Leu Glu Gly Ser Leu
                20                  25                  30

Gln Ala Arg
        35

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 34
atgcatcatc atcatcatca tgaaggtggc cgc                                    33

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met His Gly Gly Arg
 1               5
```